(12) United States Patent
Larder et al.

(10) Patent No.: US 7,235,387 B2
(45) Date of Patent: *Jun. 26, 2007

(54) METHOD FOR MUTATION DETECTION IN HIV-1 USING POL SEQUENCING

(75) Inventors: Brendan Larder, Cambridgeshire (GB); Sharon Kemp, Cambridgeshire (GB); Stuart Bloor, Cambridge (GB); Ann Brophy, Cambridge (GB)

(73) Assignee: Virco BVBA (BE)

( * ) Notice: Subject to any disclaimer, the term of this patent is extended or adjusted under 35 U.S.C. 154(b) by 271 days.

This patent is subject to a terminal disclaimer.

(21) Appl. No.: 10/258,151

(22) PCT Filed: Apr. 20, 2001
(Under 37 CFR 1.47)

(86) PCT No.: PCT/EP01/04558

§ 371 (c)(1),
(2), (4) Date: Jul. 7, 2003

(87) PCT Pub. No.: WO01/81624

PCT Pub. Date: Nov. 1, 2001

(65) Prior Publication Data

US 2005/0058981 A1    Mar. 17, 2005

Related U.S. Application Data

(63) Continuation-in-part of application No. 09/640,787, filed on Aug. 18, 2000, now Pat. No. 6,800,463.

(51) Int. Cl.
*C12Q 1/68* (2006.01)
*C12Q 1/70* (2006.01)

(52) U.S. Cl. ............... 435/91.2; 435/6; 435/5; 536/23.1; 536/23.72; 536/24.33

(58) Field of Classification Search ............ None
See application file for complete search history.

(56) References Cited

U.S. PATENT DOCUMENTS

| | | | |
|---|---|---|---|
| 5,827,648 A | 10/1998 | Eastman et al. | |
| 5,837,464 A | 11/1998 | Capon et al. | |
| 5,856,086 A | 1/1999 | Kozal et al. | |

FOREIGN PATENT DOCUMENTS

| | | | |
|---|---|---|---|
| EP | 0617 132 A2 | 9/1994 | |
| WO | WO 93/21339 | 10/1993 | |
| WO | WO 93/23574 | 11/1993 | |
| WO | WO 97/27332 | 7/1997 | |
| WO | WO 97/27480 | 7/1997 | |
| WO | WO9727480 | * 7/1997 | |
| WO | WO 98/58086 | 12/1998 | |
| WO | WO 99/58693 | 11/1999 | |
| WO | WO 99/67428 | 12/1999 | |

OTHER PUBLICATIONS

Hertogs et al. 1998. "A Rapid Method for Simultaneous Detection of Phenotypic Resistance to Inhibitors of Protease and Reverse Transcriptase in Recombinant HIV-1 Isolates from Patients . . . " Antimicrobial Agents and Chemotherapy. vol. 42, No. 2, pp. 269-276.*
Buck et al. 1999. "Design Strategies and Performance of Custom DNA Sequencing Primers." BioTechniques. vol. 27, No. 3, pp. 528-536.*
Pelemans H, et al. "Mutational analysis of Tyr-318 within the non-nucleoside reverse transcriptase inhibitor binding pocket of human immunodeficiency virus type I reverse transcriptase", JBC, 1998, 273(51): 34234-34239.*
Kemp SD, et al. "A novel polymorphism at codon 333 of human immunodeficiency virus type I reverse transcriptase can facilitate dual resistance to Zidovudine and L-2',3'-dideoxy-3'-thiacytidine", J. of Virol., 1998, 72(6):5093-5098.*
Pan et al., Detection of plasma viremia in human immunodeficiency virus-infected individuals at all clinical stages, Journal of Clinical Microbiology, 1993, vol. 31, No. 2, p. 283-288).*
Larder et al., "Quantitative Detection of HIV-1 Drug Resistance Mutations by Automated DNA Sequencing," *Nature*, vol. 365, pp. 671-673 (1993).
Demeter et al., "Interlaboratory Concordance of DNA Sequence Analysis to Detect Reverse Transcriptase Mutations in HIV-1 Proviral DNA" *Journal of Virological Methods*, '75, pp. 93-104 (1998).
Zazzi et al., "Long-Read Direct Infrared Sequencing of Crude PCR Products for Prediction of Resistance to HIV-1 Reverse Transcriptase and Protease Inhibitors," *Molecular Biotechnology*, vol. 10, pp. 1-8 (1998).
Günthard et al., "Comparative Performance of High-Density Oligonucleotide Sequencing and Dideoxynucleotide Sequencing HIV Type 1 *pol* from Clinical Samples," *Aids Research and Human Reroviruses*, vol. 14, No. 10, pp. 869-876 (1998).

(Continued)

*Primary Examiner*—Jeffrey Fredman
*Assistant Examiner*—Stephanie Mummert
(74) *Attorney, Agent, or Firm*—Yunling Ren (57) ABSTRACT

The present invention relates to a method for mutation analysis of the HIV pol gene of HIV virions comprising amplifying virion RNA or DNA via nested PCR using outer primers as represented in SEQ ID No. 1 and 2, amplifying said PCR product via nested PCR using a 5' and 3' primer chosen from the inner primers SEQ ID No. 3, 4, 5, and 6, and sequencing this secondary obtained PCR product using at least one sequencing primer chosen from any of SEQ ID No. 7 to 12 or variants thereof. In the alternative, at least one secondary sequencing primer may be used chosen from any of SEQ ID No. 13 to 24. The benefit of the sequences present in the invention resides in the fact that, with the aid of the oligonucleotides, the sequences of all presently known HIV subtypes and all mutations of the pol gene presently known to yield resistance towards antiretroviral therapy can be determined. The present invention also relates to kits for performing such a method as well as primers for performing the same.

39 Claims, 1 Drawing Sheet

OTHER PUBLICATIONS

Puchhammer-Stöck et al., "Comparison of Line Probe Assay (LIPA) and Sequence Analysis for Detection of HIV-1 Drug Resistance," Journal of Medical Virology, 57, pp. 283-289 (1999).

Duncan R. Churchill et al., "The Rabbit Study: Ritonavir and Saquinavir in Combination in Saquinavir-Experienced and Previously Untreated Patients," *Aids Research and Human Retrovirus*, vol. 15 No. 13, pp. 1181-1189 (1999).

Yerly et al., "Transmission of Antiretroviral-drug-resistant HIV-1 Variants," *The Lancet*, vol. 354, pp. 729-733 (1999).

Lorenzi et al., "Impact of Drug Resistance Mutations on Virologic Response to Salvage Therapy," *Aids*, vol. 13, No. 2, pp. F17-F21 (1999).

Schapiro et al., "Clinical Cross Resistance Between the HIV-1 Protease Inhibitors Saquinavir and Indinavir and Correlations with Genotypic Mutations," *Aids*, vol. 13, No. 3, pp. 359-365 (1999).

Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," Antimicrobial Agents and Chemotherapy, pp. 269-276 (1998).

Devereux et al., "Rapid Decline in Detectability of HIV-1 Drug Resistance Mutations After Stopping Therapy," *Aids*, vol. 13, No. 18, pp. F123-F127 (1999).

Asseline et al., "Nucleic Acid Binding Molecules with High Affinity and Base Sequence Specificity: Intercalating Agents Covalently Linked to Oligodeoxynucleotides," *Proc. Natl. Acad. Sci. USA*, 81, 3297-3301 (1984).

Barany, F., "Genetic Disease Detection and DNA Amplification Using Cloned Thermostable Ligase," *Proc. Natl. Acad. Sci USA*, 88, 189-193 (1991).

Compton, J., "Nucleic Acid Sequence-Based Amplification," *Nature*, 350, 91-92 (1991).

Duck, P., "Probe Amplifier System Based on Chimeric Cycling Oligonucleotides,": Biotechniques, 9, 142-147 (1990).

Guatelli et al., "Isothermal, In Vitro Amplification of Nucleic Acids by a Multienzyme Reaction Modeled After Retroviral Replication," *Proc. Natl. Acad. Sci. USA*, 87, 1874-1878 (1990).

Kwoh et al., "Transcription-Based Amplification System and Detection of Amplified Human Immunodeficiency Virus Type 1 with a Bead-Based Sandwich Hybridization Format," *Proc. Natl. Acad. Sci. USA*, 86, 1173-1177 (1989).

Kwok et al., Effects of Primer-template Mismatches on the Polymerase Chain Reaction: Human Immunodeficiency Views Type 1 Model Studies. *Nucl. Acids Res.*, 18, 999 (1990).

Landegren et al., A Ligase-Medicated Gene Detection Technique. *Science*, 241, 1077-1080 (1988).

Lizardi et al., "Exponential Amplification of Recombinant RNA Hybridization Probes," *Bio/Technology*, 6, 1197-1202 (1988).

Lomeli et al., "Quantitative Assays Based on the Use of Replicatable Hybridization Probes," *Clin. Chem.*, 35(9), 1826-1831 (1989).

Matsukura et al., "Phosphorothioate Analogs of Oligodeoxynucleotides: Inhibitors of Replication and Cytopathic Effects of Human Immunodeficiency Virus," *Proc. Natl. Acad. Sci. USA*, 84, 7706-7710 (1987).

Miller et al., "Nonionic Nucleic Acid Analogues. Synthesis and Characterization of Dideoxyribonucleoside Methylphosphonates," *Biochemistry*, vol. 18(23), 5134-5143 (1979).

Nielsen et al., "Sequence-Selective Recognition of DNA by Strand Displacement with a Thymine-Substituted Polyamide," *Science*, vol. 254, 1497-500 (1991).

Nielsen et al., "Sequence Specific Inhibition of DNA Restriction Enzyme Cleavage by PNA," *Nucleic-Acids-Research*, 21(2), 1997-200 (1993).

Saiki et al., "Genetic Analysis of Amplified DNA with Immobilized Sequence-Specific Oligonucleotide Probes," *Proc. Natl. Acad. Sci. USA*, vol. 86, 6230-6234 (1989).

Walker et al. "Isothermal in Vitro Amplification of DNA by a Restriction Enzyme/DNA Polymerase System," *Proc. Natl. Acad. Sci. USA*, vol. 89, 392-396 (1992).

Wu et al., "The Ligation Amplification Reaction (LAR)-Amplification of Specific DNA Sequences Using Sequential Rounds of Template-Dependent Ligation," *Genomics*, 4, 560-569 (1989).

Boom et al., "Rapid and Simple Method for Purification of Nucleic Acids," *Journal of Clinical Microbiology*, pp. 495-503 (1990).

Compton, J., "Nucleic Acid Sequence-Based Amplification," *Nature*, vol. 350, pp. 91-92 (1991).

Alexander et al., "Prevalence of primary HIV drug resistance among seroconverters during an explosive outbreak of HIV infection among injecting drug users", *AIDS*, 13, pp. 981-985, (1999).

International Search Report dated Oct. 16, 2001.

P. Kellman and B.A. Larder, "Recombinant Virus Assay: a Rapid, Phenotypic Assay for Assessment of Drug Susceptibility of Human Immunodeficiency Virus Type 1 Isolates", *Antimicrobial Agents and Chemotherapy*, 38(1), pp. 23-30, (Jan. 1994).

Kojima et al., "Changes in Viremia in Patients Receiving an Alternating or Simultaneous Regimen of AZT and DDI as Assessed by Polymerase Chain Reaction Combined with Reverse Transcription (RNA-PCR)", National Conference of Human Retrovirus and Related Infections, 1, p. 131, (1993).

Niubo et al., "Recovery and Analysis of Human Immunodeficiency Virus Type 1 (HIV) RNA Sequences from Plasma Samples with Low HIV RNA Levels", *Journal of Clinical Microbiology*, 38(1), pp. 309-312, 2000.

Sharma et al., "AZT-Related Mutation Lys70Arg in Reverse Transcriptase of Human Immunodeficiency Virus Type 1 Confers Decrease in Susceptibility to ddATP in in Vitro RT Inhibition Assay", *Virology*, 223, pp. 365-369, (1996).

Birk, et al., "Variation in HIV-1 pol gene associated with reduced sensitivity to antiretroviral drugs in treatment—naïve patients." *AIDS* (1998) vol. 12, pp. 2369-2375.

Cabana, et al., "Emergence and genetic evolution of HIV-1 variants with mutations conferring resistance to multiple reverse transcriptase and protease inhibitors" *Journal of Medical Virology* (1999) vol. 59, pp. 480-490.

Boden, et al., "HIV-1 drug resistance innewly infected individuals" *J. Am. Med. Assoc.* (1999) vol. 282, No. 12, pp. 1135-1141.

* cited by examiner

Figure 1

METHOD FOR MUTATION DETECTION IN HIV-1 USING POL SEQUENCING

CROSS REFERENCE TO RELATED APPLICATIONS

This Application is a National Stage Application under 35 U.S.C. § 371 of PCT/EP01/04558, filed Apr. 20, 2001. This application is also a continuation-in-part of and claims priority to application Ser. No. 09/640,787, filed Aug. 18, 2000, now U.S. Pat. No. 6,800,463, and EP Application No. 00201433.0, filed Apr. 20, 2000. Each of these applications are incorporated by reference in their entirety.

This application claims priority of U.S. patent application Ser. No. 09/640,787 filed Aug. 18th, 2000 and EP Patent Application No. 00201433.0 filed Apr. 18th, 2000, the contents of which are incorporated herein by reference.

FIELD OF THE INVENTION

The present invention relates to a method for detecting mutations within the HIV pol gene of HIV isolates and in particular with the design of amplification primers and sequencing primers for use in the analysis of the coding domains for the protease and reverse transcriptase, respectively.

BACKGROUND OF THE INVENTION

The rapid and specific detection of infectious agents such as HIV is of utmost importance both for the diagnosis of the infection as well as to monitor the therapy of the infected patients. In order to reduce the analytical window period, sequence based approaches are increasingly used. Detection methods based on hybridization suffer from reduced reliability because of the huge viral mutagenicity. Therefore sequencing based methods are very much desired as tools to interrogate the particular viral sequence of a biological sample.

The availability of rapid, high-throughput automated DNA sequencing technology has obvious applications in clinical research, including the detection of variations in virus populations and mutations responsible for drug resistance in virus genomes. However, analysis of clinical samples by manual sequencing or polymerase chain reaction-(PCR) based point mutation assays has revealed that complex mixtures of wild type and mutant HIV genomes can occur during drug therapy. Therefore, to assess the likely susceptibility of a virus population to a particular drug therapy, it would be desirable to perform DNA sequence analysis that can simultaneously quantitate several resistance mutations in multiple genomes. A particular advantage of analyzing the sequence of more than one pol gene enzyme (Protease and Reverse transcriptase) is that the studied material reflects to a greater extent the viral genetic diversity in the particular patient being investigated.

The main target cell for HIV infection was identified as the CD4+ subset of T-cells. In order to replicate, HIV first interacts with cells expressing the CD4 surface protein and co-receptor via binding through the gp120 envelope protein. Following fusion via the gp41 domain of the envelope, entry is achieved, the viral particle degraded and the RNA genome transcribed into double-stranded complementary DNA (cDNA). This genetic material is transported into the cell nucleus as part of the pre-integration complex, where the DNA is processed by viral integrase and incorporated into the host genome. In an activated cell, the viral genome is transcribed and subsequently translated into structural proteins and enzyme precursors. The polyproteins, Gag and Gag-Pol containing matrix, capsid, nucleocapsid as well as the enzymes reverse transcriptase, protease and integrase are directed to the cell membrane where proteolytic cleavage by viral protease and virion packaging occurs. Most of these events have been extensively studied and a number of stages for possible intervention to prevent viral replication have been identified. These include attachment and entry into the host cell, formation of proviral DNA by reverse transcriptase enzymes, integration of proviral DNA into the host cell chromosomes by integrase, as well as virus assembly, including cleavage of the precursor viral proteins, by viral protease. Clinically relevant agents have been developed against two of the viral genes, reverse transcription and protease.

The efficacy of these compounds is largely depending on the mutations present in these proteins. HIV has no proofreading mechanisms and therefore has a high mutagenic power. This high mutagenic capacity enables the virus to induce resistance the therapy by the introduction of mutations in those genes.

Retroviral inhibitors may block viral replication in various ways. For example, Nucleoside Reverse Transcriptase Inhibitors (NRTIs), compete with the natural nucleoside triphosphates for incorporation into elongating viral DNA by reverse transcriptase. Chemical modifications that distinguish these compounds from natural nucleosides result in DNA chain termination events. NRTIs that are currently available include for instance zidovudine (ZDV), didanosine (ddI), zalcitabine (ddC), stavudine (d4T), lamivudine (3TC) and abacavir (ABC).

Nucleotide reverse transcriptase inhibitors (NtRTIs) have the same mode of action as NRTIs, but they differ in that they are already monophosphorylated and therefore they require fewer metabolic steps. For example Adefovir (bis-POM-PMEA) and bis-POC PMPA belong to this category of treatments.

Non-Nucleoside Reverse Transcriptase inhibitor (NNRTIs) are a group of structurally diverse compounds which inhibit HIV reverse transcriptase by noncompetitive binding to or close to the active site of the viral reverse transcriptase enzyme, thereby inhibiting its activity. Available compounds in this group include for instance nevirapine (NVP), delavirdine (DLV) and efavirenz.

Protease Inhibitors (PIs) are peptidomimetic and bind to the active site of the viral protease enzyme, thereby inhibiting the cleavage of precursor polyproteins necessary to produce the structural and enzymatic components of infectious virions. PIs that are currently available include for instance saquinavir (SQV), ritonavir (RTV), indinavir (IDV) nelfinavir (NFV), amprenavir (APV) and lopinavir (ABT-378).

The options for antiretroviral therapy have improved considerably as new agents have become available. Current guidelines for antiretroviral therapy recommend a triple combination therapy regimen for initial treatment, such as one PI and 2 NRTIs or one NNRTI and 2 NRTIs. These combination regimens show potent antiretroviral activity and are referred to as HAART (highly active antiviral therapy). The introduction of HAART has resulted in a significant reduction of morbidity and mortality in HIV-1 patient populations with access to these drugs.

Assays for detection of mutations in HIV-1 are based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., AIDS 5, 137–144 (1991); Richman, D. D., et al., J. Infect. Dis. 164, 1075–1081 (1991); Gingeras, T. R., et al., J. Infect. Dis. 164, 1066–1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., J. Acq. Imm. Def. Syndr. Human Retrovirol. 9, 264–273 (1995); Holodniy, M., et al., J. Virol. 69, 3510–3516 (1995); Eastman, P. S., et al., J. Clin. Micro. 33, 2777–2780(1995).); Line Probe Assay (LiPA® HIV-11 RT, Innogenetics) (Stuyver, L., et al., Antimicrob. Agents Chemotherap. 41, 284–291 (1997).); Oligonucleotide ligation assay (Edelstein, R. et al. J. Clin Microbiol. 36(2), 569–572 (1998)) and GeneChip technology (Affymetrix) (D'Aquila, R. T. Clin. Diagnost. Virol. 3, 299–316 (1995); Fodor, S. P. A. et al., Nature 364, 555–556 (1993); Fodor, S. P. A. Nature 227, 393–395 (1997). DNA sequencing assays provide information on all nucleotides of the sequenced region. Target sequences are amplified by PCR. Sequence analysis is primarily based on the incorporation of dideoxy chain-terminating nucleotides (lacking 3' hydroxyl groups) in elongating DNA sequences and gel-electrophoretic analysis of the resulting molecules. Sequencing technologies can be semi-automated and make use of fluorescently labeled primers or ddNTPs to "read" off the sequence from a polyacrylamide gel. Novel techniques and approaches to determine mutations are being developed and are evenly well suited to determine mutations present in a sample under investigation. Other assays to determine mutations have become available e.g. Invader® assay (Third Wave Technologies, Inc.), WAVES® DNA assay (Transgenomic, Inc.), mass spectrometry (Jackson P., et al. Molecular Medicine Today 6, 271–276, (2000)) and surface plasmon resonance (Nakatani, K. et al. Nature Biotechnology 19(1), 18–19, (2001). An overview of currently used mutation techniques, comprising gel based and non-gel based analyses are surveyed in Shi, M. Clin. Chem. 2001, (47:2) 164–172. Sequence analysis may be performed on either nucleic acid material not limited to DNA and RNA.

Viruses devoid of proofreading mechanisms have a high mutagenic power. This mutagenic capacity provides the infectious agent with a means to escape drug treatment, by changing the drug targets. This leads to reduced drug efficacy, resistance and thus increased patient morbidity and mortality. One approach to detect the viral resistance towards pharmacological treatment involves the determination of those mutations occurring in the viral genome. In order to determine these mutations several approaches are available. Hybridization based methods (differential hybridization, BioChips, LiPa®, primer specific PCR) have been developed, however, these methods suffer from the disadvantage that only a limited set of mutations can be screened per analytical run.

Alternatively, sequencing methods have been developed. Although this technology increases reliability when compared to hybridization methods, the current protocols do not allow to reliably and within an acceptable analytical window period sequence a gene such as the HIV pol gene with all its mutations which may occur during viral mutagenesis under treatment pressure. Therefore the diagnostic value of existing sequencing methods is limited whereas the need for fast, reliable and complete sequence analysis methods is high in the field of HIV diagnostics.

The present invention concerns an improved sequencing method involving a set of primers providing a means to amplify and sequence the pol gene comprising all mutations. In addition, the present method also allows the analysis of mixed samples. The primer combination of the present invention reduces the analytical period since all mutations can be sequenced in a single laboratory format, avoiding the necessary step of additional cloning or resequencing part of the viral genome in order to identify all mutations related to drug resistance. Resequencing of the genome becomes necessary when due to viral mutagenesis, a defined primer does not hybridize properly to its target sequence. This delays the laboratory turnaround time. Using the protocol of the present invention the sequence of the sample is reliably determined on a single day. Therefore the method and the primer combination of the present invention improve the monitoring of drug resistance, leading to an improved patient management.

The aim of the present invention is thus to provide a reliable sequence analysis method and kit for performing mutation analysis of the pol gene of HIV virus isolates.

The pol gene of HIV codes for different proteins including protease, reverse transcriptase, integrase.

The present invention relates to a method for mutation analysis of the HIV pol gene of a HIV virion comprising the steps of:

a) isolation of a sample,
b) virion RNA extraction of the isolated sample material,
c) amplifying RNA via nested PCR using outer primers as represented in SEQ ID No. 1 (OUT3) and 2 (PRTO-5),
d) amplifying said PCR product via nested PCR using a 5' and 3' primer chosen from the inner primers as represented in SEQ ID No. 3 (PCR2.5), 4 (PCR2.3), 5 (SK107) and 6 (SK108), and
e) sequencing this secondary obtained PCR product using at least one sequencing primer chosen from any of SEQ ID No. 7 to 12 (Seq1FOR, Seq2FOR, Seq3F, Seq1B, Seq3B, Seq6R, Seq1F, Seq2A, Seq3A, Seq5A, Seq7A, Seq2B, Seq4B, Seq6B, Seq7B, Seq4A, Seq6A, Seq5B; see Table 1).

The present invention describes a mutation analysis of the pol gene of HIV. It should be appreciated that the group of HIV viruses contains several families HIV-1 and HIV-2. HIV-1 is present throughout the world whereas HIV-2 is widespread in West-Africa. HIV-1 isolates including group M and group O viruses, in particular group M viruses. Mixed populations carrying mutations can be detected when present down to at least 20%.

The present invention also provides a method for mutation analysis of the HIV pol gene of HIV isolates comprising the steps of:

a) isolation of a sample,
b) viral DNA extraction of the isolated sample material,
c) amplifying DNA via nested PCR using outer primers as represented in SEQ ID No. 1 (OUT3) and 2 (PRTO-5),
d) amplifying said PCR product via nested PCR using a 5' and 3' primer chosen from the inner primers as represented in SEQ ID No. 3 (PCR2.5), 4 (PCR2.3), 5 (SK107) and 6 (SK108), and
e) sequencing this secondary obtained PCR product using at least one sequencing primer chosen from any of SEQ ID No. 7 to 12 (Seq1FOR, Seq2FOR, Seq3F, Seq1B, Seq3B, Seq6R, Seq1F, Seq2A, Seq3A, Seq5A, Seq7A, Seq2B, Seq4B, Seq6B, Seq7B, Seq4A, Seq6A, Seq5B; see Table 1).

According to a preferred method said secondary PCR product is sequenced using a primer as represented in SEQ ID No. 7 (Seq1FOR).

According to a preferred method said secondary PCR product is sequenced using a primer as represented in SEQ ID No. 8 (Seq2FOR).

According to a preferred method said secondary PCR product is sequenced using a primer as represented in SEQ ID No. 9 (Seq3F).

According to a preferred method said secondary PCR product is sequenced using a primer as represented in SEQ ID No. 10 (Seq1B).

According to a preferred method said secondary PCR product is sequenced using a primer as represented in SEQ ID No. 11 (Seq3B).

According to a preferred method said secondary PCR product is sequenced using a primer as represented in SEQ ID No. 12 (Seq6R).

The present invention also provides a method according to the present invention wherein one of the initial sequencing primers is replaced by one or a pair of replacement primers (Table 2). For example, if Seq2FOR (SEQ ID No. 8) failed it is replaced by Seq3A (SEQ ID No. 15) and Seq5A (SEQ ID No. 16). However in principle any described primer that obtains sequence from the region that Seq2FOR (SEQ ID No. 8) was expected to cover can be used i.e. Seq3A (SEQ ID No. 15), Seq4A (SEQ ID No. 22) or Seq5A (SEQ ID No. 16) (see FIG. 1). In addition, Seq6A (SEQ ID No.23) and Seq5B (SEQ ID No. 24) were also not proposed to replace a specific initial primer but can be used to cover respective sequence domains (see FIG. 1).

In preferred methods according to the present invention the initial sequencing primer as represented in SEQ ID No 7 (Seq1FOR) is replaced by a primer set as represented in SEQ ID No. 13 (Seq1F) and 14 (Seq2A).

In preferred methods according to the present invention the initial sequencing primer as represented in SEQ ID No 8 (Seq2FOR) is replaced by a primer set as represented in SEQ ID No. 15 (Seq3A) and 16 (Seq5A).

In preferred methods according to the present invention the initial sequencing primer as represented in SEQ ID No 9 (Seq3F) is replaced by a primer set as represented in SEQ ID No. 16 (Seq5A) and 17 (Seq7A).

In preferred methods according to the present invention the initial sequencing primer as represented in SEQ ID No 10 (Seq1B) is replaced by a primer set as represented in SEQ ID No. 4 (PCR2.3) and 18 (Seq2B).

In preferred methods according to the present invention the initial sequencing primer as represented in SEQ ID No 11 (Seq3B) is replaced by a primer set as represented in SEQ ID No. 18 (Seq2B) and 19 (Seq4B).

In preferred methods according to the present invention the initial sequencing primer as represented in SEQ ID No 12 (Seq6R) is replaced by a primer set as represented in SEQ ID No. 20 (Seq6B) and 21 (Seq7B).

Preferably, the methods according to present invention involve a sequencing step wherein said secondary PCR product is sequenced using a primer as represented in SEQ ID No 13 (Seq1F).

Preferably, the methods according to present invention involve a sequencing step wherein said secondary PCR product is sequenced using a primer as represented in SEQ ID No 14 (Seq2A).

Preferably, the methods according to present invention involve a sequencing step wherein said secondary PCR product is sequenced using a primer as represented in SEQ ID No 15 (Seq3A).

Preferably, the methods according to present invention involve a sequencing step wherein said secondary PCR product is sequenced using a primer as represented in SEQ ID No 16 (Seq5A).

Preferably, the methods according to present invention involve a sequencing step wherein said secondary PCR product is sequenced using a primer as represented in SEQ ID No 17 (Seq7A).

Preferably, the methods according to present invention involve a sequencing step wherein said secondary PCR product is sequenced using a primer as represented in SEQ ID No 18 (Seq2B).

Preferably, the methods according to present invention involve a sequencing step wherein said secondary PCR product is sequenced using a primer as represented in SEQ ID No 19 (Seq4B).

Preferably, the methods according to present invention involve a sequencing step wherein said secondary PCR product is sequenced using a primer as represented in SEQ ID No 20 (Seq6B).

Preferably, the methods according to present invention involve a sequencing step wherein said secondary PCR product is sequenced using a primer as represented in SEQ ID No 21 (Seq7B).

Preferably, the methods according to present invention involve a sequencing step wherein said secondary PCR product is sequenced using a primer as represented in SEQ ID No 22 (Seq4A).

Preferably, the methods according to present invention involve a sequencing step wherein said secondary PCR product is sequenced using a primer as represented in SEQ ID No 23 (Seq6A).

Preferably, the methods according to present invention involve a sequencing step wherein said secondary PCR product is sequenced using a primer as represented in SEQ ID No 24 (Seq5B).

The invention further relates to primers having at least 80% sequence similarity to the sequences represented in SEQ ID 1–24, preferably at least 90% sequence similarity to the sequences represented in SEQ ID 1–24, more preferably at least 95% sequence similarity to the sequences represented in SEQ ID 1–24

The invention further relates to primers comprising at least 8 consecutive nucleotides, wherein said sequence of at least 8 consecutive nucleotides is present in SEQ ID No. 1–24

A primer acts as a point of initiation for synthesis of a primer extension product that is complementary to the nucleic acid strand to be copied. The place of hybridization is determined by the primer- and target sequence. As known by the skilled person in the art, specificity of the annealing can be guaranteed by choosing a sequence domain within the target sequence, which is unique, compared to other non-target sequences. Nevertheless, start and stop of the primer onto the target sequence may be located some nucleotides up- or downstream the defined primer site without interfering with this specificity.

Consequently, the present invention also provides a method as described above wherein the sequencing primer is chosen up to 1, 2, 3 or 4 nucleotides upstream or downstream the described primer region.

The present invention also provides a method as described above wherein the outer primer is chosen up to 1, 2, 3 or 4 nucleotides upstream or downstream the described primer region.

The present invention also provides a method as described above wherein the inner primer is chosen up to 1, 2, 3 or 4 nucleotides upstream or downstream the described primer region.

The present invention also provides a method as described above wherein the sample contains free virion particles or virus infected cells.

In particular, the present invention also provides a method as described above wherein the sample is any biological material taken either directly from the infected human being (or animal), or after culturing (e.g. for enrichment). Biological material may be e.g. expectorations of any kind, broncheolavages, blood (plasma, serum), skin tissue, biopsies, sperm, semen, lymphocyte blood culture material, colonies, liquid cultures, fecal samples, urine etc.

In one embodiment of the present invention, a biological sample is taken of a human being or animal treated or being treated with antiretroviral drug regimens.

The present invention also relates to a primer as described above (see Table 1) and used to analyze the sequence of the HIV pol gene of HIV isolates.

Preferentially, such methods according to the present invention involve the sequencing of the defined primary PCR product.

In an embodiment the present invention relates to a method as described above, wherein the mutation identified confers resistance to an antiretroviral drug.

In a further embodiment the present invention relates to a method as described above, wherein the mutation identified confers resistance to a protease inhibitor.

In one embodiment the present invention relates to a method as described above, wherein the mutation identified confers resistance to a reverse transcriptase inhibitor.

In one embodiment the present invention relates to a method as described above, wherein the mutation identified confers resistance to an integrase inhibitor.

The present invention also relates to a diagnostic kit for the mutation analysis of the HIV pol gene of HIV-1 isolates comprising at least one of the primers as shown in Table 1. The following definitions serve to illustrate the terms and expressions used in the present invention.

The term "drug-induced mutation" means any mutation different from consensus wild-type sequence, more in particular it refers to a mutation in the HIV protease or RT coding region that, alone or in combination with other mutations, confers a reduced susceptibility of the isolate to the respective drug.

The term "target sequence" as referred to in the present invention describes the nucleotide sequence of the wild type, polymorphic or drug induced variant sequence of the protease and RT gene of HIV-1 isolates to be specifically detected by sequence analysis according to the present invention. This nucleotide sequence may encompass one or several nucleotide changes. Target sequences may refer to single nucleotide positions, nucleotides encoding amino acids or to sequence spanning any of the foregoing nucleotide positions. In the present invention said sequence often includes one or two variable nucleotide positions. Sequence alterations detected by the present method include but are not limited to single nucleotide mutations, substitutions, deletions, insertions, inversions, repeats or variations covering multiple variations, optionally present at different locations. Sequence alterations may further relate to epigenetic sequence variations not limited to for instance methylation. Sequence analysis can be performed both on all types of nucleic acid including RNA and DNA.

It is to be understood that the complement of said target sequence is also a suitable target sequence in some cases.

The target material in the samples to be analyzed may either be DNA or RNA, e.g. genomic DNA, messenger RNA, viral RNA, proviral nucleic acid or amplified versions thereof. These molecules are also termed polynucleic acids. It is possible to use DNA or RNA molecules from HIV samples in the methods according to the present invention.

Well-known extraction and purification procedures are available for the isolation of RNA or DNA from a sample (e.g. in Maniatis et al., Molecular Cloning: A Laboratory Manual, $2^{nd}$ Edition, Cold Spring Harbor Laboratory Press (1989)).

The term "primer" refers to single stranded sequence-specific oligonucleotide capable of acting as a point of initiation for synthesis of a primer extension product that is complementary to the nucleic acid strand to be copied. The length and the sequence of the primer must be such that they allow priming the synthesis of the extension products.

Preferentially, the primer is about 5–50 nucleotides long. Specific length and sequence will depend on the complexity of the required DNA or RNA targets, as well on the conditions of primer use such as temperature and ionic strength.

The one skilled in the art will know that the primers of the present invention can be replaced by their complementary strands.

The fact that amplification primers do not have to match exactly with the corresponding template to warrant proper amplification is ample documented in the literature (Kwok et al. 1990).

The primers of the present invention also comprise those oligonucleotides having at least 80% similarity to the sequences in SEQ ID 1–24, preferentially at least 90% an more preferentially at least 95% similarity according to the FASTA or BLAST algorithms. (Altschul et al. "Basic local alignment search tool J. Mol. Biol. 1990, 215, 403–410, http://www.ncbi.nlm.nih.gov/blast; Lipman et al. "Rapid and sensitive protein similarity searches. Science 1985, 227, 1435–1441. http://www.ebi.ac.uk)

A "sequence similar to" a DNA sequence is not limited to any particular sequence, but is defined as such a sequence modified with substitutions, insertions, deletions, and the like known to those skilled in the art so that the function or activity of its encoded protein is substantially at the same level. Herein, "similarity" is defined as the rate (%) of identical nucleotides within a similar sequence with respect to a reference sequence. Similarity is an observable quantity that might be expressed as, for example, % identity, wherein identity means identical nucleotides. Homology refers to a conclusion drawn from these data.

Oligonucleotide generally refers to any polyribonucleotide or polydeoxribonucleotide, which may be unmodified RNA or DNA or modified RNA or DNA. Thus, for instance, oligonucleotides as used herein refer to, single-stranded DNA, or single-stranded RNA. As used herein, the term oligonucleotide includes DNAs or RNAs as described above that contain one or more modified bases. Thus, DNAs or RNAs with backbones modified for stability or for other reasons are "oligonucleotides" as that term is intended herein. Moreover, DNAs or RNAs comprising unusual bases, such as inosine, or modified bases, such as tritylated bases, to name just two examples, are oligonucleotides as the term is used herein. It will be appreciated that a great variety of modifications have been made to DNA and RNA that serve many useful purposes known to those of skill in the art. The term oligonucleotide as it is employed herein embraces such chemically, enzymatically or metabolically modified forms of oligonucleotides, as well as the chemical forms of DNA and RNA characteristic of viruses and cells, including simple and complex cells, inter alia. Polynucleotides embraces short polynucleotides often referred to as oligonucleotide(s).

There are several methods reported for amplifying nucleic acids. These methods comprise cycling techniques, isothermal reactions and combinations thereof. The amplification method used can be either polymerase chain reaction (PCR; Saiki et al. 1988), ligase chain reaction (LCR;. Landgren et al. 1988; Wu and Wallace 1989; Barany 1991), nucleic acid sequence-based amplification (NASBA; Guatelli et al. 1990; Compton 1991), transcription-based amplification system (TAS; Kwoh et al. 1989), strand displacement amplification (SDA; Duck 1990; Walker et al. 1992), rolling circle amplification (Lizardi, 1998, Zhang 1998, "Circular probe amplification using energy-transfer primers" provisional application filed) or amplification by means of Qss replicase (Lizardi et al. 1988; Lomeli et al. 1989) or any other suitable method to amplify nucleic acid molecules known in the art.

The oligonucleotides used as primer may also comprise nucleotide analogues such as phosphothiates (Matsukura et al. 1987), alkylphosphorothiates (Miller et al. 1979) or peptide nucleic acids (Nielsen et al. 1991; Nielsen et al. 1993) or may contain intercalating agents (Asseline et al. 1984).

The oligonucleotides used as primer in the sequencing reaction may also contain labels. These labels comprise but are not limited to radionucleides, fluorescent labels, biotin, chemiluminescent labels.

The oligonucleotides of the present invention may be labelled by groups enabling the capture of the amplified fragment e.g. biotin. These capture ligands enable both the detection of the nucleotides or the amplified fragment containing them and the recovery of the oligonucleotides or the amplified fragment containing them from complex mixtures.

The nucleotides used in the present invention may also be substituted by e.g. biotin, fluorescent labels or radionucleides or may contain unnatural bases.

The oligonucleotides used for the present invention can be used for the different sequencing technologies known in the art, for instance dideoxysequencing, cycle sequencing, minisequencing and any variants thereof.

FIGURES AND TABLES

The figures, tables and examples as given below exemplify the present invention. These data are not meant to limit the scope of the present invention.

Figure 1:
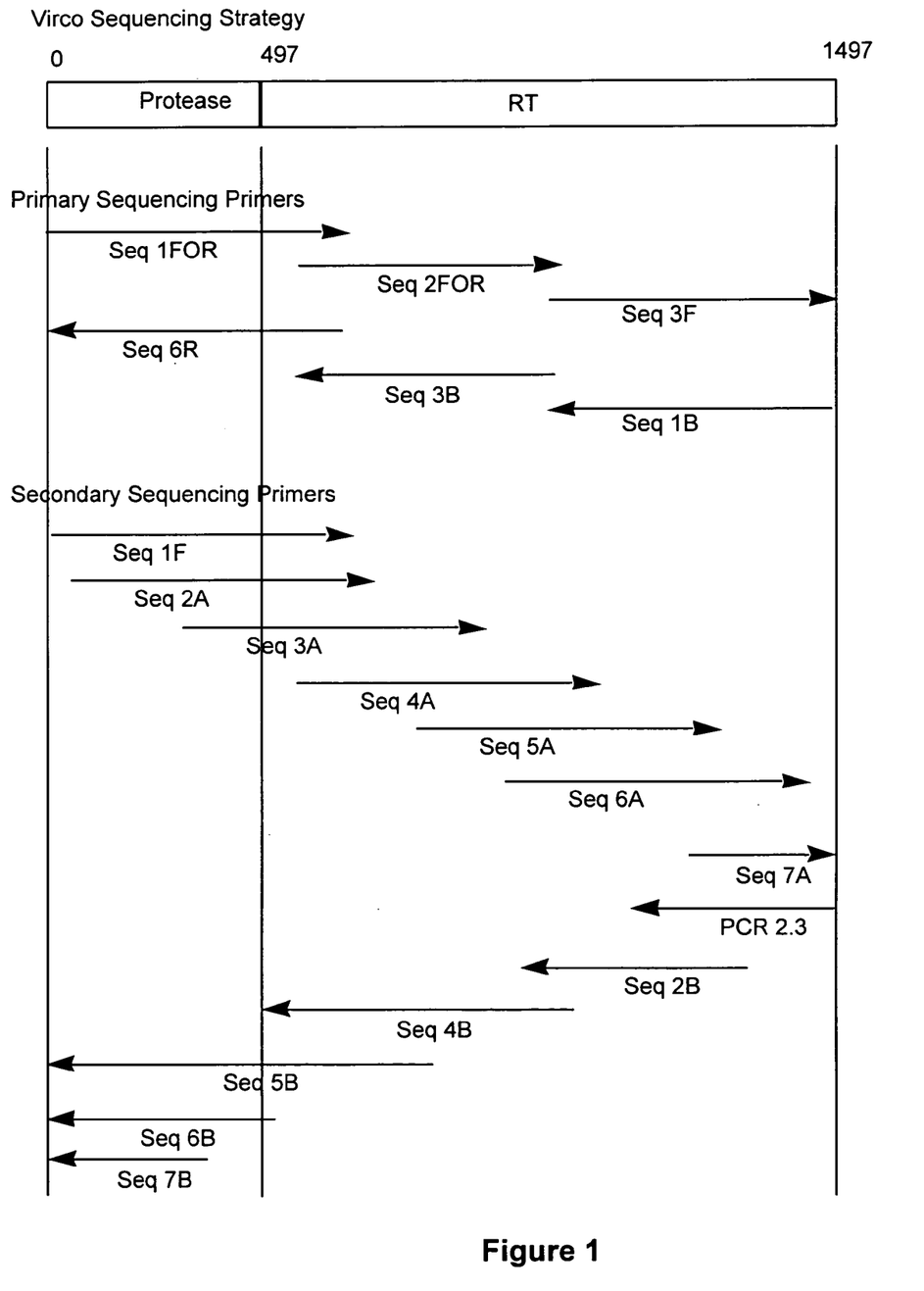
FIG. 1: Schematic overview of the total coding region of the protease-RT coding domain of HIV-1 isolates.

The protease domain is shown by a black box, the RT coding region by a shaded box. The length in nucleotides of both coding regions is indicated. Regions that are sequenced using respectively mentioned sequencing primers are shown. Primary sequences and the secondary sequences are schematically presented.

TABLE 1

Sequence of the amplification- and sequencing primers used.
Name and sequence identification numbers are indicated.

| NAME | SEQUENCE | SEQ ID N° |
|---|---|---|
| cDNA synthesis and first round PCR | | |
| OUT3 | 5'-CAT-TGC-TCT-CCA-ATT-ACT-GTG-ATA-TTT-CTC-ATG-3' | SEQ ID 1 |
| PRTO-5 | 5'GCC-CCT-AGG-AAA-AAG-GGC-TGT-TGG-3' | SEQ ID 2 |
| Second round (nested) PCR Set A | | |
| PCR2.5 | 5'-CCT-AGG-AAA-AAG-GGC-TGT-TGG-AAA-TGT-GG-3' | SEQ ID 3 |
| PCR2.3 | 5'-CTA-ACT-GGT-ACC-ATA-ATT-TCA-CTA-AGG-GAG-G-3' | SEQ ID 4 |
| Set B | | |
| SK107 | 5'-CAT-CTA-CAT-AGA-AAG-TTT-CTG-CTC-C-3' | SEQ ID 5 |
| SK108 | 5'-CTA-GGA-AAA-AGG-GCT-GTT-GGA-AAT-G-3' | SEQ ID 6 |
| Primary Sequencing primers | | |
| Seq1FOR | 5'-GAG-AGC-TTC-AGG-TTT-GGG-G-3' | SEQ ID 7 |
| Seq2FOR | 5'-AAT-TGG-GCC-TGA-AAA-TCC-3' | SEQ ID 8 |
| Seq3F | 5'-CCT-CCA-TTC-CTT-TGG-ATG-GG-3' | SEQ ID 9 |
| Seq1B | 5'-CTC-CCA-CTC-AGG-AAT-CC-3' | SEQ ID 10 |
| Seq3B | 5'-GTA-CTG-TCC-ATT-TAT-CAG-G-3' | SEQ ID 11 |
| Seq6R | 5'-CTT-CCC-AGA-AGT-CTT-GAG-TCC-3' | SEQ ID 12 |
| Secondary sequencing primers | | |
| Seq1F | 5'-CAG-ACC-AGA-GCC-AAC-AGC-CCC-3' | SEQ ID 13 |
| Seq2A | 5'-CAC-TCT-TTG-GCA-ACG-ACC-C-3' | SEQ ID 14 |

TABLE 1-continued

Sequence of the amplification- and sequencing primers used.
Name and sequence identification numbers are indicated.

| NAME | SEQUENCE | SEQ ID N° |
|---|---|---|
| Seq3A | 5'-GGT-ACA-GTA-TTA-GTA-GGA-CC-3' | SEQ ID 15 |
| Seq5A | 5'-GTA-CTG-GAT-GTG-GGT-GAT-GC-3' | SEQ ID 16 |
| Seq7A | 5'-GTG-GGA-AAA-TTG-AAT-TGG-G-3' | SEQ ID 17 |
| PCR2.3 | 5'-CTA-ACT-GGT-ACC-ATA-ATT-TCA-CTA-AGG-GAG-G-3' | SEQ ID 4 |
| Seq2B | 5'-GGG-TCA-TAA-TAC-ACT-CCA-TG-3' | SEQ ID 18 |
| Seq4B | 5'-GGA-ATA-TTG-CTG-GTG-ATC-C-3' | SEQ ID 19 |
| Seq6B | 5'-CAT-TGT-TTA-ACT-TTT-GGG-CC-3' | SEQ ID 20 |
| Seq7B | 5'-GAT-AAA-ACC-TCC-AAT-TCC-3' | SEQ ID 21 |
| Seq4A | 5'-GTA-CAG-AAA-TGG-AAA-AGG-3' | SEQ ID 22 |
| Seq6A | 5'-GGA-TGA-TTT-GTA-TGT-AGG-3' | SEQ ID 23 |
| Seq5B | 5'-GGA-TGT-GGT-ATT-CCT-AAT-TG-3' | SEQ ID 24 |

TABLE 2

Replacement or secondary sequencing primers. Initial preferred sequencing primers can be replaced by a set of possible replacement primers. Suggestions are indicated in the table.

| Initial sequencing primer | Preference set of replacement sequencing primers |
|---|---|
| Seq1FOR | Seq1F & Seq2A |
| Seq2FOR | Seq3A & Seq5A |
| Seq3F | Seq5A & Seq7A |
| Seq1B | PCR2.3 & Seq2B |
| Seq3B | Seq2B & Seq4B |
| Seq6R | Seq6B & Seq7B |

TABLE 3

Overview of mutations present in a clone used for training and validation of the assay.

| PROTEASE | REVERSE TRANSCRIPTASE |
|---|---|
| V003I | V035M |
| L010I | M041L |
| I013V | K103N |
| K020R | E122K |
| E035D | I135T |
| M036I | M184V |
| S037N | G196E |
| K043T | L210W |
| F053L | R211K |
| I054V | L214F |
| L063P | T215Y |
| I064V | P225H |
| I066F | K238T/K |
| A071V | P272A |
| V082T | T286A |
| I084V | V292I |
|  | I293V |
|  | F346Y |
|  | M357T |
|  | R358K |
|  | K366R |
|  | T376S |

Mutations were revealed according to the method of the present invention. The numbering corresponds to the exact amino acid location in either the protease or reverse transcriptase. The amino acids are represented by their one letter code. This code is well known in the art (see Alberts et.al The Molecular Biology of the Cell, 1994)

TABLE 4

On overview of patient samples comprising several mutations present in the protease and reverse transcriptase domain of HIV. Mutations were revealed according to the method of the present invention. The numbering corresponds to the exact amino acid location in either the protease or reverse transcriptase.

|  | Patient 1 | Patient 2 | Patient 3 | Patient 4 | Patient 5 | Patient 6 | Patient 7 | Patient 8 | Patient 9 | Patient 10 |
|---|---|---|---|---|---|---|---|---|---|---|
| PROTEASE | V003I | V003I | V003I | V003I | V003I | V003I | V003I | V003I | V003I | V003I |
|  | L010I | L010I | L010I | L010I | L010I | L010I | L010I | L010F/I | L010F | L010I |

TABLE 4-continued

An overview of patient samples comprising several mutations present in the protease and reverse transcriptase domain of HIV. Mutations were revealed according to the method of the present invention. The numbering corresponds to the exact amino acid location in either the protease or reverse transcriptase.

|  | Patient 1 | Patient 2 | Patient 3 | Patient 4 | Patient 5 | Patient 6 | Patient 7 | Patient 8 | Patient 9 | Patient 10 |
|---|---|---|---|---|---|---|---|---|---|---|
|  | L024I | T012K | I015V | I013V | I015V | I015V | T012A/T | I015V | I013V/I | I013V |
|  | S037N | L019V | K020R | K020I | K020T | K020V | I013V | L019I | K020R | L033F |
|  | G048M | K020R | E035D | S037N | L024F | E035D | L019I | K020I | V032I | E035D |
|  | F053L | E034Q | M036I | P039Q | S037N | S037D/N | K020R | E035D | E035D | M036I |
|  | I062V | E035D | S037K | R041K | S037D | K020R | M036I | M036I | M036I | S037N |
|  | L063P | M036I | R041N | M046I | M046I | R041R/K | E035D | S037N | S037D/N | R041K |
|  | I064V | S037N | M046I | I054V | I054L | M046I | M036I | M046I | R041K | K043T/K |
|  | E065D | R041K | L063P | I062V | I062V | G048V | S037N | I054V | K043T | I054V |
|  | I072V | G048V | H069K | L063P | L063P | F053Y | R041K | I062V | M046M/I | D060E |
|  | T074S | I054S | A071V | H069R | A071V | K045R/K | I062V | L063P | I054V | I062V |
|  | V077I | I062V | T074S | A071L | I072L | K055R/K | L063P | A071V | K055R/K | L063P |
|  | V082A | L063P | V082F | I072V | G073S | Q061H | H069H/Q | V082T | D060E | A071V |
|  |  | A071I | N088E | T074P | V077I | L063D | L089M | I084V | L063P | I072L |
|  |  | I072T/I | L089M | V077I | I084V | A071T | L090M | I085V | I064V | G073S |
|  |  | T074S | L090M | I085V/I | I085V/I | I072V | I093L/I | L090M | I072V/I | P079P/S |
|  |  | V082A | I093L | L090M | L089V | V077I |  |  | I084V | L090M |
|  |  | L090M |  | I093L | L090M | V082A |  |  | I085V/I |  |
|  |  | I093L |  |  | I093L | I085V |  |  | L090M |  |
|  |  |  |  |  |  | L090M |  |  |  |  |
|  |  |  |  |  |  | Q092K |  |  |  |  |
| REVERSE TRAN-SCRIP-TASE | P004S | I002V/I | P001P/L | K020R | M041L | M041L | V035T | K011T/K | D017D/E | P004S |
|  | K011R | V035M | K020R | A033G | K043N | K043E | M041L | K020R/K | M041L | V035I |
|  | V021I | T039A | V035T | V035L/M | E044D | E044A | K043N/K | V035A/V | K043Q | M041L |
|  | T039A | E040F | T039R | T039A | A062V | D067N | T069D/N | T039A | E044D | E044D |
|  | M041L | M041L | M041L | M041L | D067N | T069D | K070R/K | M041L | D067N | D067N |
|  | K043E | K043E | K043E | D067S/N | K070R | K102Q | E122K | E044D | V060I | T069D |
|  | E044A | D067N | E044D | K070R | L074I | V108V/I | D123E | D067N | D067G | K070R |
|  | I050T | T069D | V060I | L074I | V075T | D123E | I135V | T069D | T069D | V106I |
|  | D067D/N | V118I | D067N | V075M | K101E | I135T | K173A | V075V/M/I | L074V | F116L/F |
|  | L074I | I135T | T069D | A098G | V108I | S162C/S | Q174K | K082R/K | K103N | S162C |
|  | V075M | S162Y | A098G | K101E | V118I | I178M/I | D177E | A098G | V111I | D177E |
|  | K101Q | V179I | V118I | D123S | S162Y | V179I | Y181C | K103N | V118I | I178L |
|  | V108I | Y181C | D121H | I167V | Y181C | Y181C | G190A | V118I | D123D/N | V179V/I |
|  | V118I | M184V | I135T/I | D177E | M184V | I202V | Q207E | D121H | I135T | Y181C |
|  | D123D/E | T200E | I142V | V179I | V189V/I | H208F | L214L/F | D123S | V179A/V | Y188L |
|  | I142V | E203K | D177E | M184V | G190A | L210W | T215F/C | I142V | Y181C | T200A |
|  | S162C | Q207E | V179I/I | G190A | Q197E | R211K | L228R/H | S162C | M184V/M | Q207K |
|  | D177E | L210S | Y181C | I195L/I | H208Y | L214F | V245Q | D177E | G196E | L210W |
|  | V179I | R211K | G190G/A | G196E | L210W | T215Y | E248D | I178L | E203K | R211A |
|  | Y181C | L214F | T200A | I202V | R211K | H221Y | D250S | M184V | Q207E | L214F |
|  | M184V | T215Y | E203D | H208Y | L214F | I228H | K275R | T200A | L210W | T215Y |
|  | G190A | D218E | Q207E | L214F | T215Y | I257L | R277K | E203D | R211K | D218E |
|  | L193M | K219Q | H208F/Y | T215F | D218E | P272A | Q278H | H208Y | L214F | K219E |
|  | G196E | L228H | L210W | K219Q | K219Q | T286A/T | K281R | L210W | T215Y | P272A |
|  | T200A | V245M | R211K | L228H | L228H | A288S | T286A/T | R211K | K219R | Q278E |
|  | E203K | P272A | L214F | V245E | Q242H | I293V | E291D | L214F | K223Q | E291D |
|  | H208Y | K275Q | T215Y | R277K | P272A | Q334E | I293V | T215Y | P243T | V292I |
|  | L210W | V276T | L228H | T286P/T | R277K | G335S | E297A | V245E | V245K | I293V |
|  | R211K | L283I | V245Q | E297K | E297Q | R356K | G335D | G335S | D250E | Y318F |
|  | L214F | I293V | S251S/T | D324E | D324E | M357R | E344D/E | G335D | R277K | Q334L |
|  | T215Y | E297R/K | E291D | K347R/K | I341F | R358K | F346H/Y | R277K | I293V | P345Q |
|  | K219N | D324E | I293V | A355T | N348I | Q367E | R356K | Y318F | M357T | N348I |
|  | K223E | I329L | P294T | M357V | A360T | I375V | M357R | D324E | R358K | K350R |
|  | F227L | R356K | G335D | G359T | D364E | T376A | G359S/T | G335D | D324E | V365I |
|  | L228R | M357L | R356K | V365V/M/I | T376A | T386I | T362S/T | M357K | T376C | E370A |
|  | V245T | A360T | G359T | E370D | T377K | K390R | K366R | I375V | T377N | T376A |
|  | R277R/K | T376A | T376A | T376A | K390R | T400A | A371V | T376A | K390R | I380V/I |
|  | T286A/P | E399G | T377Q | S379C | E399D |  | T376A | T386I |  | T386I |
|  | P294Q |  | K390R | V381V/I | T400A |  | T386I | K390R |  | K390R |
|  | E297K |  | T400A | K390R |  |  | K388T | E399D |  |  |
|  | D324D/E |  |  |  |  |  | K390R |  |  |  |
|  | G359S |  |  |  |  |  |  |  |  |  |
|  | T369A |  |  |  |  |  |  |  |  |  |
|  | T376S |  |  |  |  |  |  |  |  |  |
|  | K390R |  |  |  |  |  |  |  |  |  |

EXAMPLES

The examples given below are to exemplify the present invention and not to limit the scope of the invention.

Modes for Carrying out the Invention

I. Introduction

The choice of oligonucleotides or primers for amplification and sequencing of the target nucleic acid is critical for the sensitivity and and specificity of the assay. The sequence to be amplified is usually only present in minute amounts in a complex matrix e.g. a blood sample of a patient. The primers should therefore be sufficiently complementary to the target sequence to allow efficient amplification and subsequent sequencing of the target nucleic acid. If the primers do not anneal properly to the target area, the amplification can be seriously affected, and as a consequence yield false results. It has been found that the reliability of primer dependent analyses can be further enhanced if the primer sequences meet or are optimized with respect to the following requirements: G and C content, no duplex formation between the primers, no hairpin formation within the primer(s), no false priming sites for the selected set of nucleotides, no hybridization with itself. It is evident that the requirements also concern the complementary strands. Evidence has been reported that sequencing primer do not need to match exactly the target sequence (Kwok et al. 1990).

A. Amplification of the HIV-1 Protease—Reverse Transcriptase Coding Domain

RNA was isolated from 100 μl of plasma according to the method described by Boom et al. (1990), and reverse transcribed with the GeneAmp reverse transcriptase kit (Perkin Elmer) as described by the manufacturer using a HIV-1 specific downstream primer (OUT3, see Table 1). Two subsequent nested PCR were set up using specific outer primers (PRTO-5 and OUT3) and inner primers (PCR2.5 and PCR2.3), respectively (see Table 1). The outer primer reaction was done as described in WO97/27480 and Hertogs et al. Antimicrob. Agents Chemotherap. 1998. The inner amplification was performed in a 96 well plate as follows: 4 μl of the outer amplification product was diluted to a final volume of 50 μl using a 10× amplification mix consisting of 5 μl 10× PCR buffer containing 15 mM MgCl$_2$, 1 μl dNTP's (10 mM) 0.5 μl PCR2.5 (0.25 μg/ml), 0.5 μl PCR2.3 (0.25 μg/ml), 0.4 μl Expand High Fidelity (3.5 U/μl) and MQ water. Amplification was initiated after a short denaturation of the amplification product made using the outer primers (2 min at 94° C.). 10 amplification cycles were started consisting of a 15 sec denaturation step at 94° C., a 30 sec annealing step at 60° C. and a 2 min polymerase step at 72° C., respectively. This amplification was immediately followed by 25 cycles consisting of a 15 sec denaturation step at 94° C., a 30 sec annealing step at 60° C. and a x min polymerase step at 72° C., respectively; where x started at 2 min and 5 sec and increased each cycle with 5 sec. Amplification was finalised by an additional polymerase step (7 min at 72° C.). Subsequently, the reaction was held at 4° C. till further analyzed or stored at −20° C. (for short periods) or −70° C. (for longer periods). In order to analyze the amplification products, a DNA agarose gel was run and amplification products were visualised using UV-detection. Obtained PCR products were purified using the QIAquick 96-well plate system as described by the manufacturer (Qiagen).

B. Sequencing of Pol Coding Region

The coding domain of the pol gene present on the amplified fragments was analyzed via sequencing using standard sequencing techniques. Preferentially, one started initial with a set of 6 primers (Seq1FOR, Seq2FOR, Seq3F, Seq1B, Seq3B and Seq6R) covering the coding domain of the HIV-protease and reverse transcriptase protein. Sequences and location onto the coding region are shown in Table 1 and FIG. 1, respectively. The sequencing was started by first distributing 4 μl of the primer stocks (4.0 μM) over a 96 well plate where each stock is pipetted down the column. In a second step, master mixes were made consisting of 14 μl MQ, 17.5 μl dilution buffer, 7 μl sample (PCR fragment) and 14 μl Big Dye Terminator Mix. A fraction (7.5 μl) of each master mix, containing a specific PCR fragment, was transferred to a specific place into the 96 well plate so that each sample fraction was mixed with a different PCR primer set. Samples were pipetted across the rows. Samples were placed in a thermal cycler and sequencing cycles started. The sequencing reaction consisted of 25 repetitive cycles of 10 sec at 96° C., 5 sec at 50° C. and 4 min at 60° C., respectively. Finally, sequence reactions were held at 4° C. till further analysis or stored as previously described. The sequencing reactions were precipitated using a standard ethanol precipitation procedure, resuspended in 2 μl formamide and heated for 2 minutes at 92° C. in the thermal cycler. Samples were cooled on ice until ready to load. 1 μl of each reaction was loaded on a 4.25% vertical acrylamide gel in a 377 sequencer system and gel was run until separation of the fragments was complete.

C. Sequence Analysis of Pol Coding Region

Sample sequences were imported as a specific project into the sequence manager of Sequencher (Genecodes) and compared to the wild type HXB2 Pro/RT reference sequence (e.g. HIVHXB2 sequence, Genbank sequence accession No. 327742). Sequences were assembled automatically and set at 85% minimum match. Secondary peaks were searched and the minimum was set at 60%. Any sequence that hung over the 5' end or the 3' end of the reference was deleted. When a region of overlap between sequences from the same strand was reached, the poorest quality of sequence was deleted leaving an overlap of 5–10 bases. Ambiguous base calls are considered poor matches to exact base calls. The sequence assembly was saved within a contig that can be edited.

Obtained sequences were edited so that base calls could be interpreted easily. Ambiguous sequences were retrieved and checked for possible errors or points of heterogeneity. When the point of ambiguity appeared correct (both strands of sequence agree but is different from the reference sequence) it was interpreted to be a variant. The reference sequence was used as an aid for building a contig and a guide to overall size and for trimming, but was not used for deciding base calls. A change was only made when both strands agreed. All gaps were deleted or filled, unless they occur in contiguous groups of a multiple of 3 (I.E. insertion or deletion of complete codons) based on data form both sequence strands. Once the editing was complete, the new contig sequence was saved as a consensus sequence and used for further analysis.

Detailed sequence editing was performed following certain rules: A) ABI primer blobs are trimmed at 5' ends where 1 consecutive base remain off the scale; sequence is trimmed not more than 25% until the first 25 bases contain less than 1 ambiguity; at least first 10 bases from the 5' end are removed, B) 3' ends are trimmed starting 300 bases after the 5' trim; the first 25 bases containing more than 2 ambiguities are removed; trim from 3' end until the last 25 bases contain less than 1 ambiguity. The maximum length of the obtained sequence fragment after trimming is 550 bases.

Sequences that failed to align were removed from the assembly and replaced by data retrieved from new sequence analyses. When further failures occurred, PCR reactions were repeated. Chromatograms were visualized using the IBM software system (cfr. Table 3 & 4).

D. Detection of Clonal Clinical Samples—Analysis of Limit of Detection for Heterozygous Base Calls.

A clonal clinical sample was mixed with wild type HXB2 at known ratio's to determine limits of detection of the system. The limit of detection was found to be around 1000 RNA copies/ml from plasma; mixed populations of mutations could be detected when present down to 20%.

The references cited in the specification are listed below:

Altschul S, Gish W, Miller W, Myers E., Lipman D. (1990) Basic local alignment search tool *J. Mol. Biol.*, 215, 403–410

Asseline U, Delarue M, Lancelot G, Toulme F, Thuong N (1984) Nucleic acidbinding molecules with high affinity and base sequence specificity: intercalating agents covalently linked to oligodeoxynucleotides. *Proc. Natl. Acad. Sci. USA* 81, 3297–301

Barany, F (1991). Genetic disease detection and DNA amplification using cloned thermostable ligase. *Proc. Natl. Acad. Sci USA*, 88,189–193.

Compton, J (1991). Nucleic acid sequence-based amplification. *Nature*, 350, 91–92.

Duck, P. (1990) Probe amplifier system based on chimeric cycling oligonucleotides. *Biotechniques*, 9, 142–147.

Eastman P S; Boyer E; Mole L; Kolberg J; Urdea M; Holodniy (1995) Nonisotopic hybridization assay for determination of relative amounts of genotypic human immunodeficiency virus type 1 zidovudine resistance. *J. Clin. Microbiol.*, 33(10), 2777–80.

Eastman P S; Urdea M; Besemer D; Stempien M; Kolberg J (1995) Comparison of selective polymerase chain reaction primers and differential probe hybridization of polymerase chain reaction products for determination of relative amounts of codon 215 mutant and wild-type HIV-1 populations. *J. AIDS and Hum. Retrovirol.* 9(3), 264–73.

Edelstein R E, Nickerson D A, Tube V O, Manns-Arcuino L A, Frenkel L M. (1998) Oligonucleotide ligation assay for detecting mutations in the human immunodeficiency virus type 1 pol gene that are associated with resistance to zidovudine, didanosine, and lamivudine. *J Clin Microbiol. Feb;*36(2):569–72.

Fodor S P; Rava R P; Huang X C; Pease A C; Holmes C P; Adams C L (1993) Multiplexed biochemical assays with biological chips. *Nature*, 364, 555–6.

Gingeras T R; Prodanovich P; Latimer T; Guatelli J C; Richman D D; Barringer K (1991) Use of self-sustained sequence replication amplification reaction to analyze and detect mutations in zidovudine-resistant human immunodeficiency virus. *J. Infect. Dis.*, 164(6), 1066–74.

Guatelli, J C; Whitfield, K M; Kwoh, D Y; Barringer, K J, Richman, D D; Gingeras, T R (1990). Isothermal, in vitro amplification of nucleic acids by a multienzyme reaction modeled after retroviral replication. *Proc. Natl. Acad. Sci USA*, 87, 1874–1878.

Hertogs K, de Bethune M P, Miller V, Ivens T, Schel P, Van Cauwenberge A, Van Den Eynde C, Van Gerwen V, Azijn H, Van Houtte M, Peeters F, Staszewski S, Conant M, Bloor S, Kemp S, Larder B, Pauwels R (1998) A rapid method for simultaneous detection of phenotypic resistance to inhibitors of protease and reverse transcriptase in recombinant human immunodeficiency virus type 1 isolates from patients treated with antiretroviral drugs. *Antimicrob Agents Chemother* 42(2), 269–276.

Holodniy M; Mole L; Margolis D; Moss J; Dong H; Boyer E; Urdea M; Kolberg J; Eastman S (1995) Determination of human immunodeficiency virus RNA in plasma and cellular viral DNA genotypic zidovudine resistance and viral load during zidovudine-didanosine combination therapy *J. Virol.*, 69(6), 3510–6.

Kwoh, D; Davis, G; Whitfield, K; Chappelle, H; Dimichele, L; Gingeras, T. (1989). Transcription-based amplification system and detection of amplified human immunodeficiency virus type 1 with a bead-based sandwich hybridization format. *Proc. Natl. Acad Sci USA*, 86,1173–1177.

Kwok, S., Kellog, D., McKinney, N., Spasic, D., Goda, L., Levenson, C. and Sinisky, J. (1990). Effects of primer-template mismatches on the polymerase chain reaction: Human immunodeficiency views type 1 model studies. *Nucl. Acids Res.*, 18, 999.

Landgren, U; Kaiser, R; Sanders, J; Hood, L. (1988). A ligase-mediated gene detection technique. *Science*, 241, 1077–1080

Larder B A; Kellam P; Kemp S D (1991), Zidovudine resistance predicted by direct detection of mutations in DNA from HIV-infected lymphocytes. *AIDS* 5(2), 137–44.

Lizardi, P; Guerra, C; Lomeli, H; Tussie-Tuna, I; Kramer, F (1988). Exponential amplification of recombinant RNA hybridization probes. *Bio/Technology*, 6,1197–1202.

Lipman D. Pearson W. Rapid and sensitive protein similarity searches. (1985) *Science*, 227, 1435–1441

Lomeli, H; Tyagi, S; Printchard, C; Lisardi, P; Kramer, F (1989). Quantitative assays based on the use of replicatable hybridization probes. *Clin. Chem.*, 35,1826–1831.

Maniatis et al., Molecular Cloning: A Laboratory Manual, 2$^{nd}$ Edition, Cold Spring Harbor Laboratory Press (1989)

Matsukura M, Shinozuka K, Zon G, Mitsuya H, Reitz M, Cohen J, Broder S (1987).Phosphorothioate analogs of oligodeoxynucleotides: inhibitors of replication and cytopathic effects of human immunodeficiency virus. Proc. Natl. Acad. Sci. USA, 84, 7706–10.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry, 18, 5134–43

Nielsen P, Egholm M, Berg R, Buchardt O (1991) Sequence-selective of DNA by strand displacement with a thymine-substituted polyamide. Science, 254, 1497–500

Nielsen P, Egholm M, Berg R; Buchardt O (1993) Sequence specific inhibition of DNA restriction enzyme cleavage by PNA. Nucleic-Acids-Res., 21, 197–200

Richman D D; Guatelli J C; Grimes J; Tsiatis A; Gingeras T (1991), Detection of mutations associated with zidovudine resistance in human immunodeficiency virus by use of the polymerase chain reaction. *J. Infect. Dis.* 164(6), 1075–81.

Saiki R, Walsh P, Levenson C, Erlich H. Genetic analysis of amplified DNA with immobilized sequence-specific oligonucleotide probes (1989) Proc Natl Acad Sci USA, 86, 6230–6234.

Shi M, (2001) Enabling large-scale pharmacogenetic studies by high-throughput mutation detection and genotyping technologies. *Clin Chem.* 47:164–172.

Stuyver L; Wyseur A; Rombout A; Louwagie J; Scarcez T; Verhofstede C; Rimland D; Schinazi R F; Rossau R (1997), Line probe assay for rapid detection of drug-selected mutations in the human immunodeficiency virus type 1 reverse transcriptase gene. *Antimicrobial Agents and Chemotherapy* 41(2), 284–91.

Walker, G; Little, M; Nadeau, J; Shank, D (1992). Isothermal in vitro amplification of DNA by a restriction enzyme/DNA polymerase system *Proc. Natl. Acad. Sci USA,* 89, 392–396.

Wu, D; Wallace, B. (1989). The ligation amplification reaction (LAR)-amplification of specific DNA sequences using sequential rounds of template-dependent ligation. *Genomics,* 4, 560–569.

What is claimed is:

1. A method for mutation analysis of the pol gene of HIV-1 isolates comprising the steps of:
   a) isolation of a sample,
   b) virion RNA extraction of the isolated sample material
   c) amplifying RNA via nested PCR using outer primers as represented in SEQ ID No.1 and 2 to obtain a primary PCR product,
   d) amplifying said primary PCR product via nested PCR using a 5' and 3' primer chosen from the inner primers as represented in SEQ ID No. 3, 4, 5 and 6, and
   e) sequencing this secondary obtained PCR product using at least one sequencing primer chosen from any of SEQ ID No. 7 to 12;
   wherein at least one of the sequencing primers is replaced by one or a pair of replacement primers having at least 90% similarity to SEQ ID No. 7 to 12 and wherein the replacement primers obtain a sequence from the region that the at least sequencing primer is expected to cover.

2. A method for mutation analysis of the pol gene of HIV-1 isolates comprising the steps of:
   a) isolation of a sample,
   b) viral DNA extraction of the isolated material
   c) amplifying DNA via nested PCR using outer primers as represented in SEQ ID No.1 and 2 to obtain a primary PCR product,
   d) amplifying said primary PCR product via nested PCR using a 5' and 3' primer chosen from the inner primers as represented in SEQ ID No. 3, 4, 5 and 6, and
   e) sequencing this secondary obtained PCR product using at least one sequencing primer chosen from any of SEQ ID No. 7 to 12;
   wherein at least one of the sequencing primers is replaced by one or a pair of replacement primers having at least 90% similarity to SEQ ID No. 7 to 12 and wherein the replacement primers obtain a sequence from the region that the at least sequencing primer is expected to cover.

3. The method of claim 1 wherein the sequencing primer is chosen up to 1, 2, 3 or 4 nucleotides upstream or downstream the described primer region.

4. The method of claim 1 wherein the outer primer is chosen up to 1, 2, 3 or 4 nucleotides upstream or downstream the described primer region.

5. The method of claim 1 wherein the inner primer is chosen up to 1, 2, 3 or 4 nucleotides upstream or downstream the described primer region.

6. The method of claim 1 wherein the sample contains free virion particles or virus infected cells.

7. The method of claim 1 wherein the sequencing is performed on the primary PCR product.

8. The method of claim 1 wherein the mutation identified confers resistance to an antiretroviral.

9. The method of claim 1 wherein the mutation identified confers resistance to a protease inhibitor.

10. The method of claim 1 wherein the mutation identified confers resistance to a reverse transcriptase inhibitor.

11. The method of claim 1 wherein the mutation identified confers resistance to a integrase inhibitor.

12. The method of claim 2 wherein one of the initial sequencing primers is replaced by one or a pair of replacement primers.

13. The method of claim 2 wherein the sequencing primer is chosen up to 1, 2, 3 or 4 nucleotides upstream or downstream the described primer region.

14. The method of claim 2 wherein the outer primer is chosen up to 1, 2, 3 or 4 nucleotides upstream or downstream the described primer region.

15. The method of claim 2 wherein the inner primer is chosen up to 1, 2, 3 or 4 nucleotides upstream or downstream the described primer region.

16. The method of claim 2 wherein the sample contains free virion particles or virus infected cells.

17. The method of claim 3 wherein the sample contains free virion particles or virus infected cells.

18. The method of claim 4 wherein the sample contains free virion particles or virus infected cells.

19. The method of claim 5 wherein the sample contains free virion particles or virus infected cells.

20. The method of claim 2 wherein the sequencing is performed on the primary PCR product.

21. The method of claim 3 wherein the sequencing is performed on the primary PCR product.

22. The method of claim 4 wherein the sequencing is performed on the primary PCR product.

23. The method of claim 5 wherein the sequencing is performed on the primary PCR product.

24. The method of claim 2 wherein the mutation identified confers resistance to an antiretroviral.

25. The method of claim 3 wherein the mutation identified confers resistance to an antiretroviral.

26. The method of claim 4 wherein the mutation identified confers resistance to an antiretroviral.

27. The method of claim 5 wherein the mutation identified confers resistance to an antiretroviral.

28. The method of claim 2 wherein the mutation identified confers resistance to a protease inhibitor.

29. The method of claim 3 wherein the mutation identified confers resistance to a protease inhibitor.

30. The method of claim 4 wherein the mutation identified confers resistance to a protease inhibitor.

31. The method of claim 5 wherein the mutation identified confers resistance to a protease inhibitor.

32. The method of claim 2 wherein the mutation identified confers resistance to a reverse transcriptase inhibitor.

33. The method of claim 3 wherein the mutation identified confers resistance to a reverse transcriptase inhibitor.

34. The method of claim 4 wherein the mutation identified confers resistance to a reverse transcriptase inhibitor.

35. The method of claim 5 wherein the mutation identified confers resistance to a reverse transcriptase inhibitor.

36. The method of claim 2 wherein the mutation identified confers resistance to an integrase inhibitor.

37. The method of claim 3 wherein the mutation identified confers resistance to an integrase inhibitor.

38. The method of claim 4 wherein the mutation identified confers resistance to an integrase inhibitor.

39. The method of claim 5 wherein the mutation identified confers resistance to an integrase inhibitor.

* * * * *

UNITED STATES PATENT AND TRADEMARK OFFICE
CERTIFICATE OF CORRECTION

PATENT NO. : 7,235,387 B2  Page 1 of 1
APPLICATION NO. : 10/258151
DATED : July 7, 2003
INVENTOR(S) : Brendan Larder et al.

It is certified that error appears in the above-identified patent and that said Letters Patent is hereby corrected as shown below:

Column 16,
Line 58, delete "form" and insert -- from --.

Column 17,
Line 13, delete "ratio's" and insert -- ratios --.
Line 44, delete "Tube" and insert -- Tobe --.

Column 18,
Line 27, delete "Tuna" and insert -- Luna --.

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO.         : 7,235,387 B2
APPLICATION NO.    : 10/258151
DATED              : June 26, 2007
INVENTOR(S)        : Brendan Larder et al.

Page 1 of 1

It is certified that error appears in the above-identified patent and that said Letters Patent is hereby corrected as shown below:

Column 16,
Line 58, delete "form" and insert -- from --.

Column 17,
Line 13, delete "ratio's" and insert -- ratios --.
Line 44, delete "Tube" and insert -- Tobe --.

Column 18,
Line 27, delete "Tuna" and insert -- Luna --.

This certificate supersedes the Certificate of Correction issued November 18, 2008.

Signed and Sealed this

Ninth Day of December, 2008

JON W. DUDAS
*Director of the United States Patent and Trademark Office*

```
                              SEQUENCE LISTING

<160> NUMBER OF SEQ ID NOS: 24

<210> SEQ ID NO 1
<211> LENGTH: 33
<212> TYPE: DNA
<213> ORGANISM: Human immunodeficiency virus type 1

<400> SEQUENCE: 1
cattgctctc caattactgt gatatttctc atg                                    33

<210> SEQ ID NO 2
<211> LENGTH: 24
<212> TYPE: DNA
<213> ORGANISM: Human immunodeficiency virus type 1

<400> SEQUENCE: 2
gcccctagga aaagggctg ttgg                                               24

<210> SEQ ID NO 3
<211> LENGTH: 29
<212> TYPE: DNA
<213> ORGANISM: Human immunodeficiency virus type 1

<400> SEQUENCE: 3
cctaggaaaa agggctgttg gaaatgtgg                                         29

<210> SEQ ID NO 4
<211> LENGTH: 31
<212> TYPE: DNA
<213> ORGANISM: Human immunodeficiency virus type 1

<400> SEQUENCE: 4
ctaactggta ccataatttc actaagggag g                                      31

<210> SEQ ID NO 5
<211> LENGTH: 25
<212> TYPE: DNA
<213> ORGANISM: Human immunodeficiency virus type 1

<400> SEQUENCE: 5
catctacata gaaagtttct gctcc                                             25

<210> SEQ ID NO 6
<211> LENGTH: 25
<212> TYPE: DNA
<213> ORGANISM: Human immunodeficiency virus type 1

<400> SEQUENCE: 6
ctaggaaaaa gggctgttgg aaatg                                             25

<210> SEQ ID NO 7
<211> LENGTH: 19
<212> TYPE: DNA
<213> ORGANISM: Human immunodeficiency virus type 1

<400> SEQUENCE: 7
gagagcttca ggtttgggg                                                    19
```

<210> SEQ ID NO 8
<211> LENGTH: 18
<212> TYPE: DNA
<213> ORGANISM: Human immunodeficiency virus type 1

<400> SEQUENCE: 8
aattgggcct gaaaatcc                                                    18

<210> SEQ ID NO 9
<211> LENGTH: 20
<212> TYPE: DNA
<213> ORGANISM: Human immunodeficiency virus type 1

<400> SEQUENCE: 9
cctccattcc tttggatggg                                                  20

<210> SEQ ID NO 10
<211> LENGTH: 17
<212> TYPE: DNA
<213> ORGANISM: Human immunodeficiency virus type 1

<400> SEQUENCE: 10
ctcccactca ggaatcc                                                     17

<210> SEQ ID NO 11
<211> LENGTH: 19
<212> TYPE: DNA
<213> ORGANISM: Human immunodeficiency virus type 1

<400> SEQUENCE: 11
gtactgtcca tttatcagg                                                   19

<210> SEQ ID NO 12
<211> LENGTH: 21
<212> TYPE: DNA
<213> ORGANISM: Human immunodeficiency virus type 1

<400> SEQUENCE: 12
cttcccagaa gtcttgagtc c                                                21

<210> SEQ ID NO 13
<211> LENGTH: 21
<212> TYPE: DNA
<213> ORGANISM: Human immunodeficiency virus type 1

<400> SEQUENCE: 13
cagaccagag ccaacagccc c                                                21

<210> SEQ ID NO 14
<211> LENGTH: 19
<212> TYPE: DNA
<213> ORGANISM: Human immunodeficiency virus type 1

<400> SEQUENCE: 14
cactctttgg caacgaccc                                                   19

<210> SEQ ID NO 15
<211> LENGTH: 20
<212> TYPE: DNA
<213> ORGANISM: Human immunodeficiency virus type 1

<400> SEQUENCE: 15
ggtacagtat tagtaggacc                                              20

<210> SEQ ID NO 16
<211> LENGTH: 20
<212> TYPE: DNA
<213> ORGANISM: Human immunodeficiency virus type 1

<400> SEQUENCE: 16
gtactggatg tgggtgatgc                                              20

<210> SEQ ID NO 17
<211> LENGTH: 19
<212> TYPE: DNA
<213> ORGANISM: Human immunodeficiency virus type 1

<400> SEQUENCE: 17
gtgggaaaat tgaattggg                                               19

<210> SEQ ID NO 18
<211> LENGTH: 20
<212> TYPE: DNA
<213> ORGANISM: Human immunodeficiency virus type 1

<400> SEQUENCE: 18
gggtcataat acactccatg                                              20

<210> SEQ ID NO 19
<211> LENGTH: 19
<212> TYPE: DNA
<213> ORGANISM: Human immunodeficiency virus type 1

<400> SEQUENCE: 19
ggaatattgc tggtgatcc                                               19

<210> SEQ ID NO 20
<211> LENGTH: 20
<212> TYPE: DNA
<213> ORGANISM: Human immunodeficiency virus type 1

<400> SEQUENCE: 20
cattgtttaa cttttgggcc                                              20

<210> SEQ ID NO 21
<211> LENGTH: 18
<212> TYPE: DNA
<213> ORGANISM: Human immunodeficiency virus type 1

<400> SEQUENCE: 21
gataaaacct ccaattcc                                                18

<210> SEQ ID NO 22
<211> LENGTH: 18
<212> TYPE: DNA
<213> ORGANISM: Human immunodeficiency virus type 1

<400> SEQUENCE: 22
gtacagaaat ggaaaagg                                                18

<210> SEQ ID NO 23
<211> LENGTH: 18
<212> TYPE: DNA
<213> ORGANISM: Human immunodeficiency virus type 1

<400> SEQUENCE: 23

```
ggatgatttg tatgtagg                                                    18

<210> SEQ ID NO 24
<211> LENGTH: 20
<212> TYPE: DNA
<213> ORGANISM: Human immunodeficiency virus type 1

<400> SEQUENCE: 24
ggatgtggta ttcctaattg                                                  20
```